(12) United States Patent
Tuomela

(10) Patent No.: US 9,080,994 B2
(45) Date of Patent: Jul. 14, 2015

(54) ANALYTE SENSOR WITH SPENT GAS FLUSHED ENDCAPS

(71) Applicant: MOCON, INC., Minneapolis, MN (US)

(72) Inventor: Stephen D. Tuomela, Ramsey, MN (US)

(73) Assignee: Mocon, Inc., Minneapolis, MN (US)

( * ) Notice: Subject to any disclaimer, the term of this patent is extended or adjusted under 35 U.S.C. 154(b) by 302 days.

(21) Appl. No.: 13/649,479

(22) Filed: Oct. 11, 2012

(65) Prior Publication Data

US 2014/0102914 A1    Apr. 17, 2014

(51) Int. Cl.
*G01N 33/00*    (2006.01)

(52) U.S. Cl.
CPC .................................. *G01N 33/0027* (2013.01)

(58) Field of Classification Search
CPC .......... G01N 33/0004; G01N 33/0027; G01N 33/044; G01N 27/404–27/4078
USPC .................. 204/400, 409, 424, 431; 205/781, 205/783.5–785, 787; 73/23.31, 23.32
See application file for complete search history.

(56) References Cited

U.S. PATENT DOCUMENTS

| 3,318,577 | A | 5/1967 | Banks |
| 3,933,174 | A | 1/1976 | Kanomata |
| 4,341,370 | A | 7/1982 | Banks |
| 5,386,965 | A | 2/1995 | Marchal |
| 2006/0124457 | A1* | 6/2006 | Mayer et al. .................. 204/424 |
| 2007/0181837 | A1* | 8/2007 | Mayer et al. .................. 251/122 |

FOREIGN PATENT DOCUMENTS

EP    1416206 A2    6/2004

* cited by examiner

*Primary Examiner* — J. Christopher Ball
*Assistant Examiner* — Maris R Kessel
(74) *Attorney, Agent, or Firm* — Sherrill Law Offices, PLLC

(57) ABSTRACT

A sensor for detecting a target analyte in a gaseous sample at ultra-low concentrations wherein access opening(s) provided through the sensor housing are plugged with endcap(s) and spent gas (i.e., gaseous sample post detection) is channeled along the interface between the sensor housing and the endcap(s) prior to venting of the spent gas, for flushing any environmentally introduced target analyte from this interface.

18 Claims, 6 Drawing Sheets

ANALYTE SENSOR WITH SPENT GAS FLUSHED ENDCAPS

BACKGROUND

A wide variety of sensors have been developed and employed for detecting and measuring the presence of various analytes in a sample, such as water vapor and oxygen. One of the more cost effective and reliable types of analyte sensors are the electrochemical sensors (i.e., sensors employing an electrolytic cell with an anode, cathode and electrolyte).

Although the balance of the description provided herein is directed to electrochemical sensors, and specifically to water vapor sensors, the invention is equally applicable to other types of sensors for detecting other types of analytes wherein an inert carrier gas is employed to transport target analyte into operable engagement with the sensor.

Electrochemical sensors for detecting and measuring a target analyte such as water-vapor or oxygen are well known and widely used. However, the construction and design of these sensors severely limit the accuracy, sensitivity, responsiveness and service life of these sensors.

U.S. Pat. Nos. 5,184,392 and 7,569,128 disclose oxygen and water vapor electrochemical sensor that provide significantly improved accuracy, sensitivity, responsiveness and service life relative to previously known sensors, but a continuing need exists in certain industry segments for a cost-effective sensor capable of even further improved sensitivity.

SUMMARY OF THE INVENTION

A first aspect of the invention is a sensor for detecting a target analyte, such as water vapor or oxygen, in a gaseous sample. The sensor comprises (a) a container defining an enclosed space and with at least one access opening, (b) a stopper sealingly engaged within each access opening, (c) a target analyte detection assembly retained within the enclosed space, (d) an inlet and an outlet configured and arranged for introducing an externally delivered test gas into sensible engagement with the target analyte detection assembly to create spent gas, and discharging the spent gas from the target analyte detection mechanism to atmosphere, and (e) a channel system interconnecting the inlet and outlet, configured and arranged to direct spent gas through a peripheral passageway at the interface of the container and each stopper prior to discharge of the spent gas to atmosphere.

In a preferred embodiment the target analyte detection assembly consumes the vast majority of target analyte in the test gas flowing through the target analyte detection assembly so as to produce spent gas having a greatly depleted concentration of target analyte.

A second aspect of the invention is a method of measuring the concentration of a target analyte, such as water vapor or oxygen, in a gaseous sample using a sensor in accordance with the first aspect of the invention. The method includes the steps of (i) effecting a continuous flow of test gas into sensing communication with the target analyte detection assembly through the inlet in the sensor, and (ii) measuring the concentration of target analyte in the test gas with the target analyte detection assembly.

DETAILED DESCRIPTION OF A PREFERRED EMBODIMENT

Nomenclature

10 Sensor
20 Housing
21 First Longitudinal End of Housing
22 Second Longitudinal End of Housing
28 Lumen Defined by Housing
28x Longitudinal Axis of Lumen
29 Chamber Defined by Housing Between First Endcap and Support Plate
29$_1$ Inlet Orifice
29$_2$ Outlet Orifice
30 Frame
40 First Endcap
41 Longitudinal Post Extending Inward from First Endcap
43' Peripheral Inner O-ring
43" Peripheral Outer O-ring
49$_1$ Inlet Orifice in First Endcap
49$_2$ Annular Peripheral Channel in First Endcap
49$_3$ Outlet Orifice in First Endcap
50 Second Endcap
51 Inlet O-ring
52 Inlet Tube
53' Peripheral Inner O-ring
53" Peripheral Outer O-ring
59$_1$ Return Gas Inlet Orifice in Second Endcap
59$_2$ Annular Peripheral Channel in Second Endcap
60 Return Tube
70 Detection Assembly
80 Spring
90 Support Plate
91 Longitudinal Post Extending Inward from Support Plate
99 Circumferential Passageway Around Support Plate
100 Sensor
120 Housing
121 First Longitudinal End of Housing
122 Second Longitudinal End of Housing
128 Lumen Defined by Housing
129 Chamber Defined by Housing
129$_1$ Inlet Channel
129$_2$ Outlet Channel
140 Endcap
143' Peripheral Inner O-ring
143" Peripheral Outer O-ring
143''' Peripheral Outermost O-ring
149$_1$ Inlet Channel in Endcap
149$_2$ Primary Annular Peripheral Channel in Endcap
149$_3$ Secondary Annular Peripheral Channel in Endcap
149$_4$ Diversion Channel to Secondary Annular Peripheral Channel in Endcap
160 Exhaust Tube 170 Detection Assembly
r Radial Direction
x Longitudinal Axis

Definitions

As utilized herein, including the claims, the phrase "spent gas" means a gas containing a depleted concentration of a target analyte as a result of consumption of the target analyte by a coulometric target analyte sensor.

Description

Construction

Figure 1:
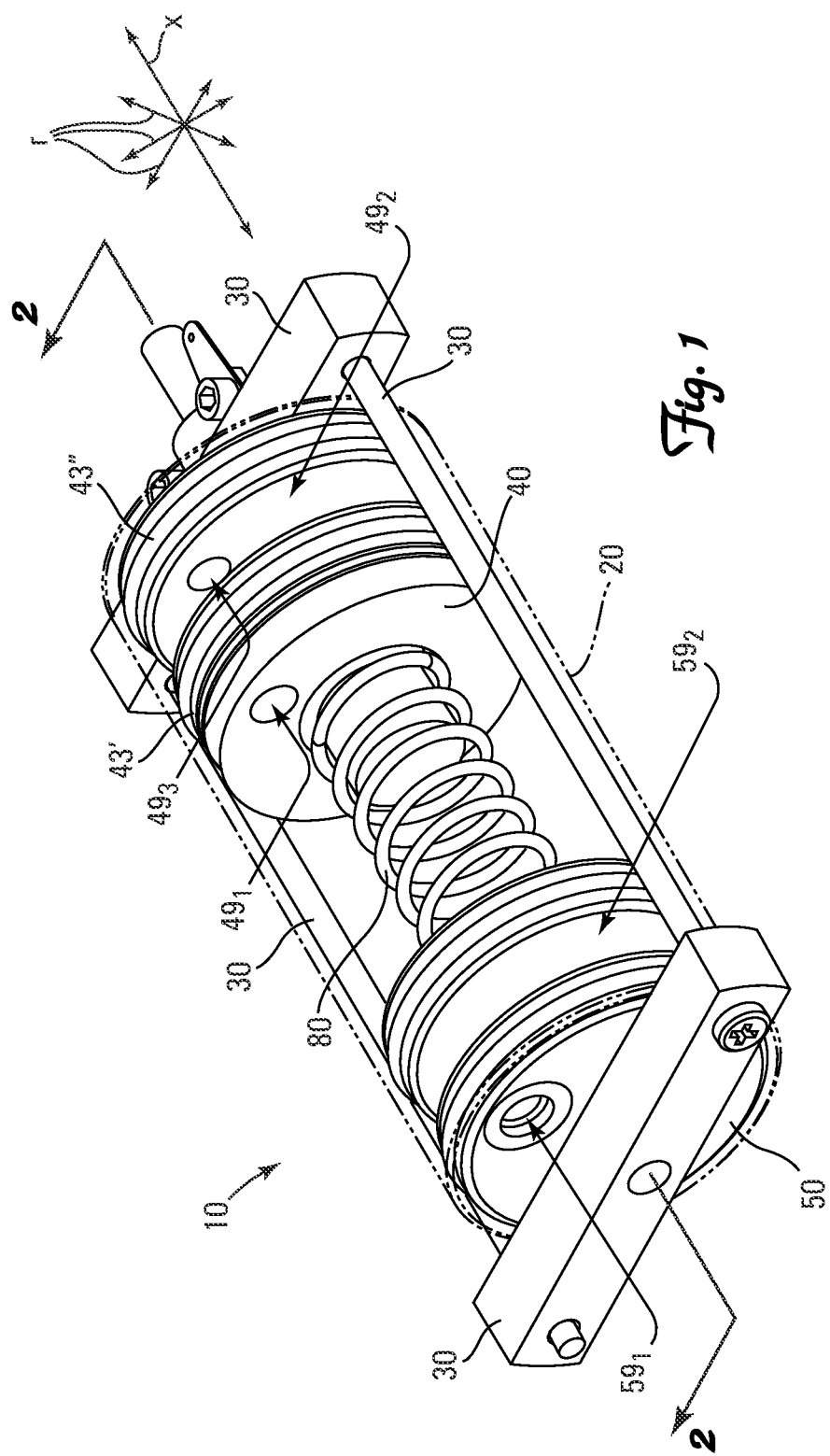
FIG. 1 is a perspective view of one embodiment of the invention sans return tube.
Figure 2:
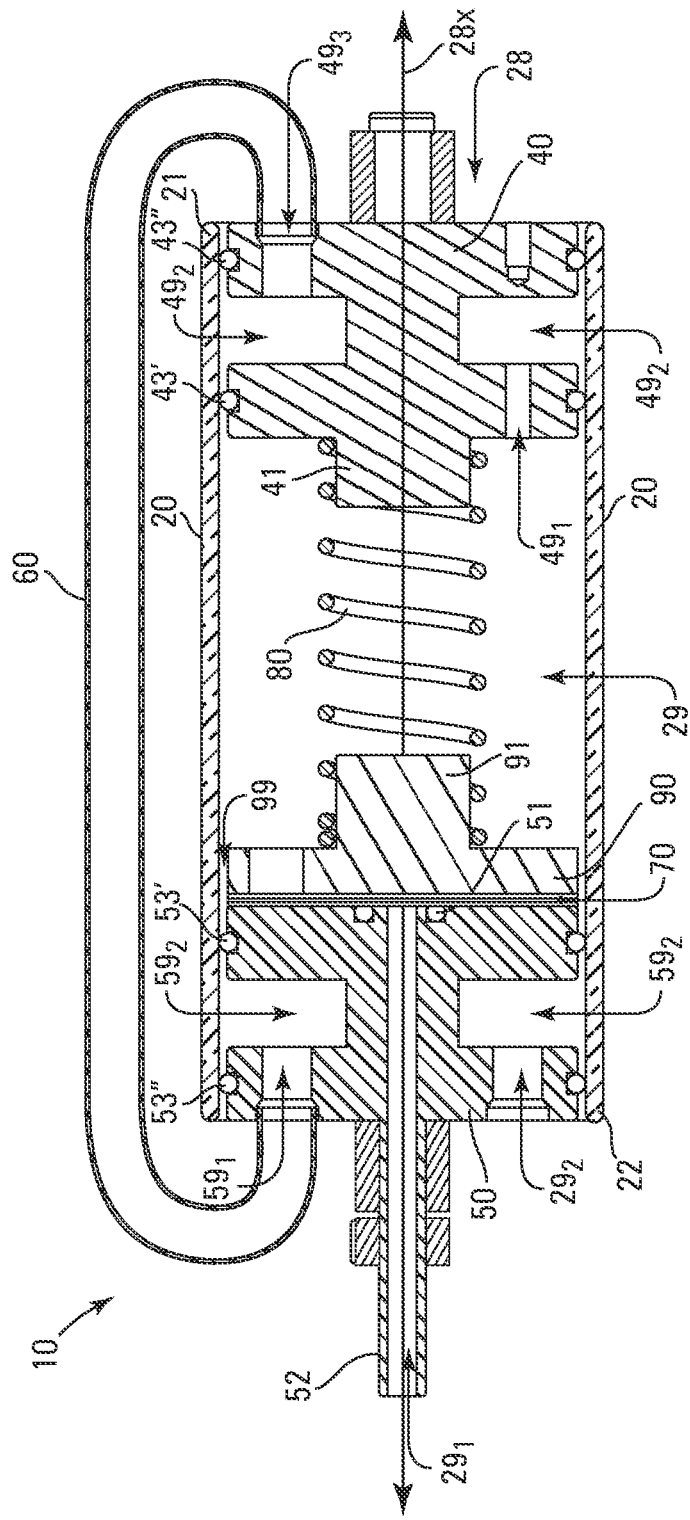
FIG. 2 is a cross-sectional side view of the invention shown in FIG. 1 taken along line 2-2 with return tube.
Figure 3:
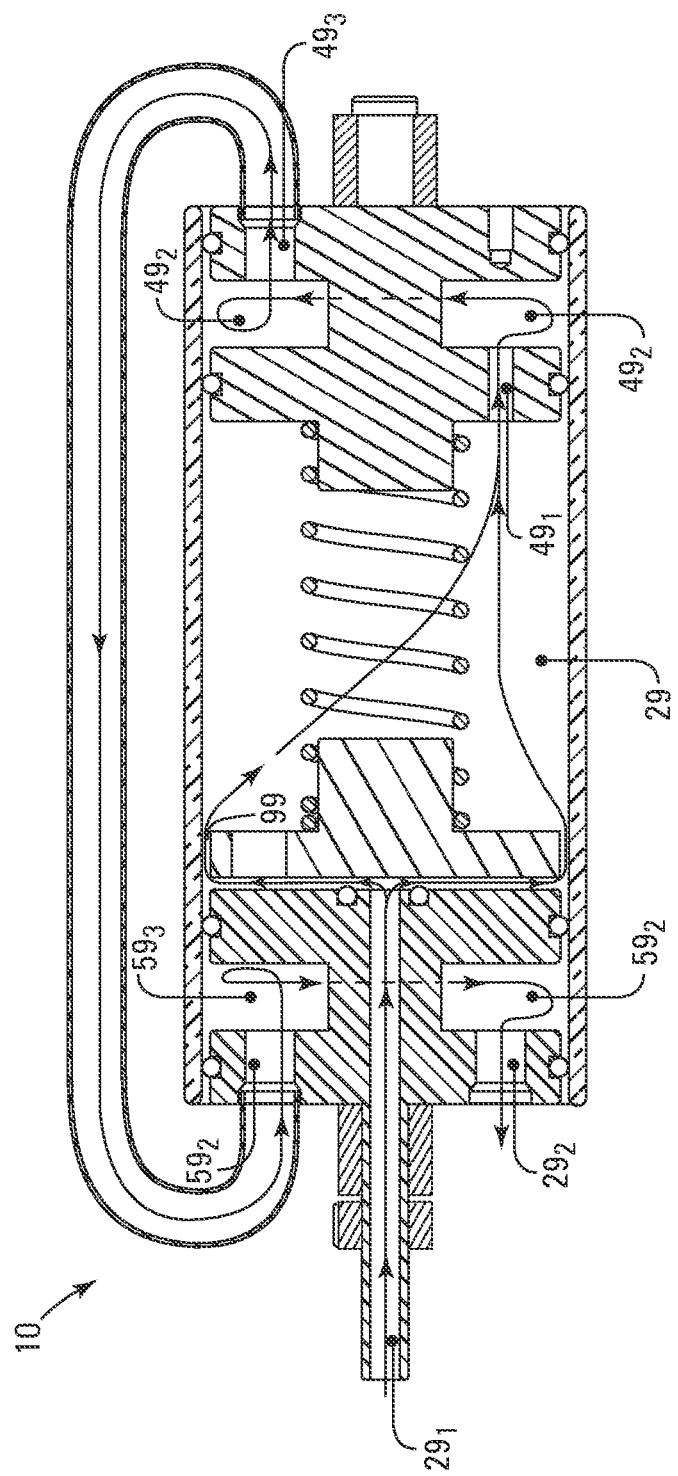
FIG. 3 is the cross-sectional side view of the invention shown in FIG. 2 sans detection assembly for purposes of facilitating depiction of gas flow through the sensor.
Figure 4:
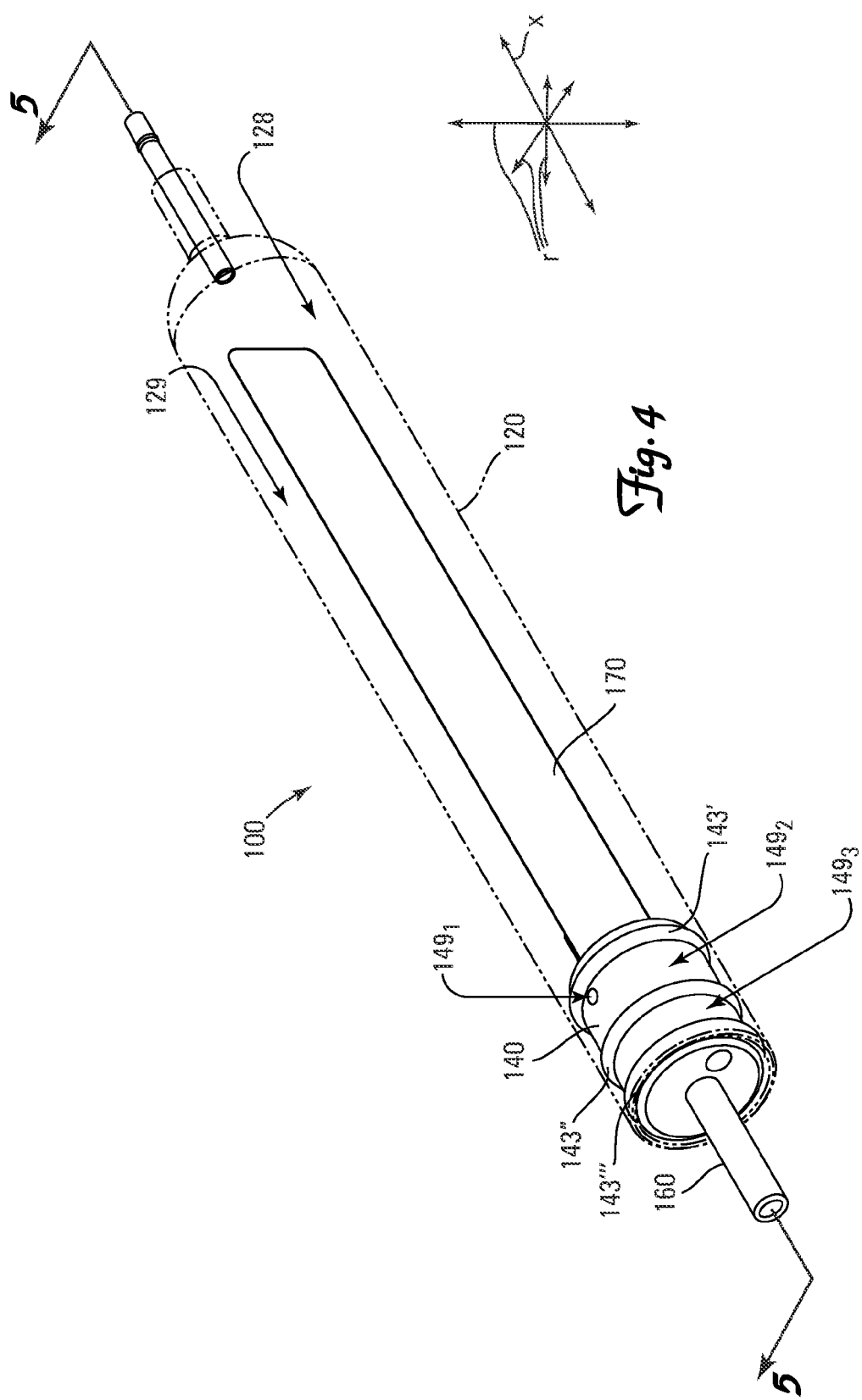
FIG. 4 is a perspective view of another embodiment of the invention.
Figure 5:
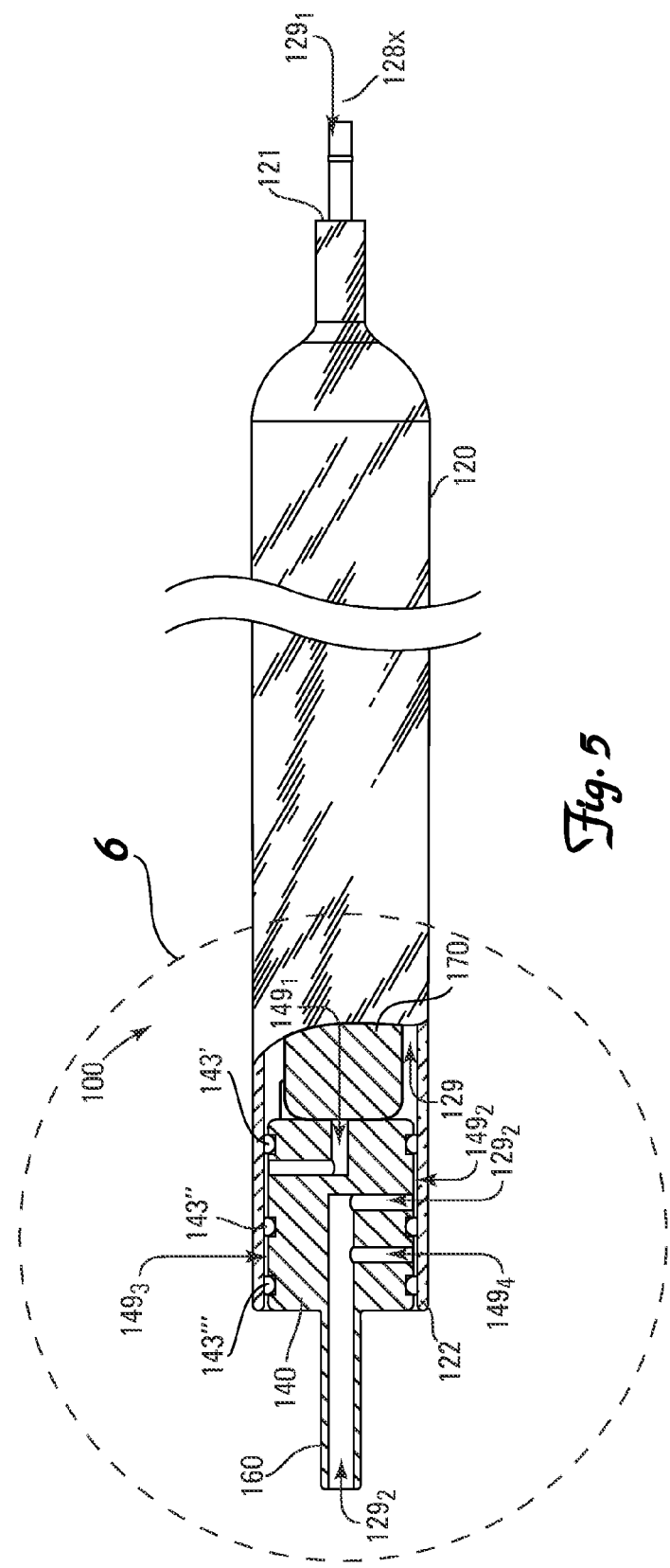
FIG. 5 is a cross-sectional side view of the invention shown in FIG. 4 taken along line 5-5.
Figure 6:
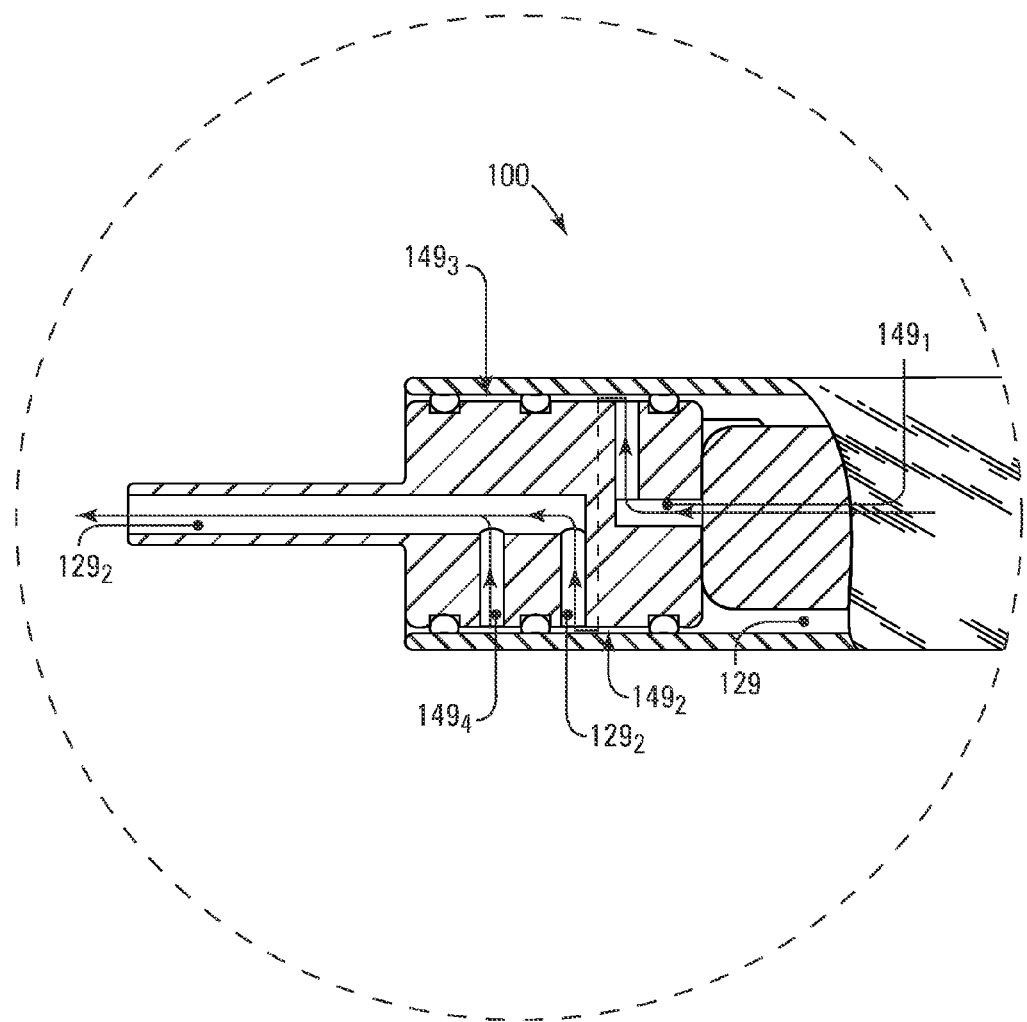
FIG. 6 is an enlarged cross-sectional side view of the outlet end of the invention shown in FIG. 5 for purposes of facilitating depiction of gas flow through the sensor.

The invention is a sensor 10 or 100 for detecting a target analyte (not shown), such as water vapor or oxygen, in a gaseous sample (not shown). One embodiment is depicted in FIGS. 1-3, while a second embodiment is depicted in FIGS. 4-6. These embodiments shall be described separately.

Dual Flushed Endcaps (FIGS. 1-3)

Referring to the embodiment depicted in FIGS. 1-3, the sensor 10 includes a detection assembly 70 retained in a fixed position within a housing or container 20 by a retention system (not collectively numbered). The housing 20 has two access openings (not numbered), one at each longitudinal end 21 and 22 of the housing 20. Each of the access openings is sealingly plugged by an endcap or stopper 40 and 50 respectively. The sensor 10 has an inlet $29_1$ for introducing a test gas into sensible engagement with the target analyte detection assembly 70 within the housing 20, and an outlet $29_2$ for discharging the spent gas to atmosphere. The inlet $29_1$ and outlet $29_2$ are fluidly interconnected by a channel system (not collectively numbered) that is configured and arranged to direct spent gas through peripheral passageways $49_2$ and $59_2$ at the interface of the housing 20 and each endcap 40 and 50, respectively, prior to discharge of the spent gas to atmosphere.

Housing 20

As shown in FIGS. 1-3, the housing 20 has a lumen 28 that forms a chamber 29 for sealingly and protectively surrounding the components of the sensor 10—particularly the detection assembly 70—while permitting controlled flow of a gaseous sample to be tested (test gas) into contact with the detection assembly 70. The housing 20 may have any desired size and shape effective for achieving these functions, including the hollow cylinder or tube shape as shown in FIGS. 1-3.

The housing 20 may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Glass is generally preferred due to its highly inert and stable nature, electrical insulative properties, and the fact that it is highly impermeable to most target analytes of interest such as water vapor and oxygen.

Retention System

As shown in FIGS. 1-3, the detection assembly 70 may be conveniently held in place within the lumen 28 of the housing 20 by a retention system (not collectively numbered). The retention system includes (i) a frame 30, (ii) a first endcap 40 sealingly engaged within a first access opening (not numbered) at the first longitudinal end 21 of the housing 20, (iii) a second endcap 50 sealingly engaged within a second access opening (not numbered) at the second longitudinal end 22 of the housing 20, (iv) a support plate 90 proximate the interior surface (not numbered) of the second endcap 50 for supporting the detection assembly 70 against the interior surface (not numbered) of the second endcap 50, and (v) a compressed compression spring 80 between the first endcap 40 and the support plate 90.

Frame 30

As shown in FIGS. 1-3, a frame 30 is provided for retaining the components in a fixed, dimensionally stable position relative to one another. The frame 30 may be constructed from the same materials as the housing 20, with a preference for machineable structural plastics such as Delrin™ available from Dupont.

Endcaps 40 and 50

As shown in FIGS. 1-3, the endcaps 40 and 50 are attached to the housing 20 at the longitudinal ends 21 and 22 of the housing 20 in such a manner that the endcaps 40 and 50 sealingly plug access openings (not numbered) at each longitudinal end 21 and 22, respectively, and will remain in a longitudinally x fixed position when subjected to an outwardly directed longitudinal force after assembly of the sensor 10.

The first endcap 40 provides an inwardly projecting longitudinal post 41 for engaging and retaining an end (unnumbered) of the spring 80. The first endcap 40 also has a pair of longitudinally x spaced, peripheral o-rings—an inner o-ring 43' and an outer o-ring 43"—operable for sealingly engaging the inside surface (not numbered) of the housing 20 and preventing potentially contaminating fluid flow from the surrounding environment into chamber 29 along the peripheral interface between the housing 20 and the first endcap 40.

The second endcap 50 similarly has a pair of longitudinally x spaced, peripheral o-rings—an inner o-ring 53' and an outer o-ring 53"—operable for sealingly engaging the inside surface (not numbered) of the housing 20 and preventing potentially contaminating fluid flow from the surrounding environment into chamber 29 along the peripheral interface between the housing 20 and the second endcap 50.

The endcaps 40 and 50 are preferably constructed from a material that is highly impermeable to the target analyte of interest, with a strong preference for a metal such as stainless steel.

Return Tube 60

As shown in FIG. 2, a return tube 60 is provided for directing spent gas exiting the first endcap 40 through an outlet orifice $49_3$ to a return gas inlet orifice $59_1$ in the second endcap 50 so that the spent gas can be utilized at both access openings to flush any environmentally introduced target analyte that has penetrated through or around the respective outer peripheral o-ring 43" and 53" respectively, before it can penetrate through or around the respective inner peripheral o-ring 43' and 53', respectively.

The return tube 60 may be constructed from any suitably inert material which can form an effective seal with the first and second endcaps 40 and 50, and will not excessively contaminate spent gas passing through the return tube 60. A variety of suitable materials known to those skilled the art may be used, with a preference for stainless steel based upon the highly inert nature of stainless steel.

Spring 80 and Support Plate 90

As shown in FIGS. 1-3, an outwardly directed longitudinal x biasing force is provided by a compressed compression spring 80 concentrically positioned about the longitudinal axis 28x of the lumen 28. The spring 80 is held in position between the first endcap 40 and a support plate 90 positioned proximate the interior surface (not numbered) of the second endcap 50. The support plate 90 is configured and arranged so that the plate 90 will longitudinally x slide within the lumen 28 and thereby transmit the outwardly directed longitudinal x biasing force of the spring 80 onto the detection assembly 70 positioned between the support plate 90 and the second endcap 50.

The support plate 90 is configured and arranged to create a circumferential passageway 99 between the inner surface (unnumbered) of the housing 20 and the periphery of the support plate 90 so that a gaseous sample centrally delivered into the detection assembly 70 will flow radially r through the separator 70 to the outer periphery (unnumbered) of the detection assembly 70, through the circumferential passageway 99 around the support plate 90, and into the chamber 29 between the first and second endcaps 40 and 50 respectively.

One option for creating a circumferential passageway 99 around the support plate 90 is to provide at least three uniformly-spaced and radially-extending projections (not shown) around the periphery of the support plate 90. These projections (not shown), such as raised bumps, contact the inner surface (unnumbered) of the housing 20 and thereby space the periphery of the support plate 90 a small distance from the inner surface (unnumbered) of the housing 20 to create the circumferential passageway 99.

The spring 80 preferably exerts an outwardly directed force of between about 5 to about 20 psi. A force of less than about 5 psi does not provide sufficient force to ensure dimensional stability of the detection assembly 70 while a force of greater than about 20 psi may crush one or more components of the detection assembly 70.

The first endcap 40 and support plate 90 each have a centrally positioned, longitudinally x extending post 41 and 91, respectively, for engaging and retaining the ends (unnumbered) of the spring 80.

The spring 80 may be constructed from any material capable of providing the necessary elastic biasing force with plastic and metallic springs generally preferred.

The support plate 90 may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Metals, such as steel, are generally preferred based upon the high structural integrity, low cost and generally inert nature of most metals.

Since both the spring 80 and the support plate 90 are wholly retained within the housing 20 (i.e., are not exposed to the surrounding atmosphere) nor contacted by test gas until after target-analyte in the test gas has been consumed and depleted by the detection assembly 70 (i.e., contacted only by spent gas), these components may be constructed from materials which are target-analyte permeable. However, to avoid even the remotest possibility that target-analyte may be absorbed or adsorbed into these components and out-gassed during testing, even these components are preferably made of a metal such as stainless steel.

Detection Assembly 70

As shown in FIGS. 1-3, a detection assembly 70 is retained within the lumen 28 of the housing 20. The detection assembly 70 is sandwiched between the second endcap 50 and the support plate 90. A detailed description of a suitable detection assembly 70 is provided in U.S. Pat. No. 7,569,128, the disclosure of which is hereby incorporated by reference. Briefly, a typical detection assembly 70 includes an anode (not individually shown), a cathode (not individually shown), and an electrolyte (not individually shown) intermediate the anode and cathode. The gaseous sample under investigation flows into the detection assembly 70 where target anlayte within the test gas is detected and consumed as a result of the detection process. The target-analyte depleted test gas, now referenced as spent gas, exits the detection assembly 70 and is then directed throughout the sensor 10 by a channel system (not collectively numbered).

Channel System

As shown in FIGS. 2 and 3, a series of orifices (not collectively numbered) and channels (not collectively numbered) are provided in various components of the sensor 10 for (i) directing test gas into operable sensing contact with the detection assembly 70, (ii) directing spent gas to "flush" the peripheral interface between the housing 20 and the endcaps 40 and 50, and finally (iii) discharging the spent flush gas from the sensor 10 to atmosphere.

Referring to FIG. 3, fluid flows through the channel system (not collectively numbered) in the following sequence:

Test gas is introduced into the sensor 10 and into sensing engagement with the detection assembly 70 through an inlet orifice $29_1$ defined by an inlet tube 52 in the second endcap 50 and past an inlet o-ring 51 provided at the interface of the second endcap 50 and the detection assembly 70, The test gas flows radially r through the detection assembly 70 where target analyte in the test gas is detected and consumed, forming target analyte depleted spent gas, The spent gas peripherally exits the detection assembly 70 and flows through a circumferential or peripheral gap 99 between the inner wall (unnumbered) of the housing 20 and the periphery of the support plate 90, The spent gas then flows within the chamber 29 from the periphery of the support plate 90 to an inlet orifice $49_1$ in the inner surface (unnumbered) of the first endcap 40, From the inlet orifice $49_1$ the spent gas flows around the periphery of the first endcap 40 at the interface of the inner surface (unnumbered) of the housing 20 and the outer surface (unnumbered) of the first endcap 40 within an annular peripheral channel $49_2$ located between inner and outer o-rings 43' and 43", and then exits the first endcap 40 and the lumen 28 of the housing 20 through an outlet orifice $49_3$ in the first endcap 40 which is radially r diametrically located relative to the inlet orifice $49_1$ in the first endcap 40, Spent gas exiting the first endcap 40 is directed by return tube 60 from the outlet orifice $49_3$ in the first endcap 40 to a return gas inlet orifice $59_1$ in the second endcap 50, From the inlet orifice $59_1$ the spent gas flows around the periphery of the second endcap 50 at the interface of the inner surface (unnumbered) of the housing 20 and the outer surface (unnumbered) of the second endcap 50 within an annular peripheral channel $59_2$ located between inner and outer o-rings 53' and 53", and is then vented to atmosphere from the second endcap 50 and the lumen 28 of the housing 20 through an outlet orifice $29_2$ in the second endcap 40 which is radially r diametrically located relative to the return gas inlet orifice $59_1$ in the second endcap 40.

If desired, a tube (not shown) may be connected to outlet orifice $29_2$ for directing spent gas exiting the second endcap 50 through outlet orifice $29_2$ for capture and subsequent treatment or for venting from a room or building.

Single Flushed Endcap (FIGS. 4-6)

Referring to the embodiment depicted in FIGS. 4-6, the sensor 100 includes a detection assembly 170 retained in a fixed position within a housing or container 120. The housing 120 has one access opening (unnumbered) at the second longitudinal end 122 of the housing 120. The access opening is sealingly plugged by an endcap or stopper 140. The sensor 100 has an inlet $129_1$ at the first longitudinal end 121 of the housing 120 for introducing a test gas into sensible engagement with the target analyte detection assembly 170 within the housing 120, and an outlet $129_2$ at the second longitudinal end 122 of the housing 120 for discharging the spent gas to atmosphere. The inlet $129_1$ and outlet $129_2$ are fluidly interconnected by a channel system (not collectively numbered) that is configured and arranged to direct spent gas through at least one peripheral passageway $149_2$ at the interface of the housing 120 and the endcap 140 prior to discharge of the spent gas to atmosphere.

Housing 120

As shown in FIGS. 4-6, the housing 120 has a lumen 128 that forms a chamber 129 for sealingly and protectively surrounding the components of the sensor 100—particularly the detection assembly 170—while permitting controlled flow of a gaseous sample to be tested (test gas) into contact with the detection assembly 170. The housing 120 may have any desired size and shape effective for achieving these functions, including the hollow cylinder or tube shape as shown in FIGS. 4-6.

The housing 120 may be constructed from any material possessing sufficient structural integrity, including specifically, but not exclusively, metals such as aluminum, copper, zinc and steel, plastics such as polyethylene, polypropylene, polyvinyl chloride and polyurethane, glass, wood, etc. Glass is generally preferred due to its highly inert and stable nature, electrical insulative properties, and the fact that it is highly impermeable to most target analytes of interest such as water vapor and oxygen.

Endcap 140

As shown in FIGS. 1-3, a single endcap 140 is attached to the housing 120 at the second longitudinal end 122 of the housing 120 in such a manner that the endcap 140 sealingly plug the access opening (unnumbered) in the second longitudinal end 122.

The first endcap 140 has a pair of longitudinally x spaced, peripheral o-rings—an inner o-ring 143' and an outer o-ring 143"—operable for sealingly engaging the inside surface (not numbered) of the housing 120 and preventing potentially contaminating fluid flow from the surrounding environment into chamber 129 along the peripheral interface between the housing 120 and the first endcap 140.

The first endcap 140 has an additional outermost peripheral o-ring 143'" for providing further protection against contaminating fluid flow from the surrounding environment into chamber 129 along the peripheral interface between the housing 120 and the first endcap 140.

The first endcap 140 forms an exhaust tube 160 that extends outward from the endcap 140 away from the sensor lumen 128 of the housing 120.

The endcap 140 is preferably constructed from a material that is highly impermeable to the target analyte of interest, with a strong preference for a metal such as stainless steel.

Detection Assembly 70

As shown in FIGS. 1-4, a detection assembly 170 is retained within the lumen 128 of the housing 120. A detailed description of a suitable detection assembly 170 for detection of oxygen is provided in U.S. Pat. No. 5,184,392, the disclosure of which is hereby incorporated by reference. Briefly, a typical detection assembly 170 includes an anode (not individually shown), a cathode (not individually shown), and an electrolyte (not individually shown) intermediate the anode and cathode. The gaseous sample under investigation flows into the detection assembly 170 where target anlayte within the test gas is detected and consumed as a result of the detection process. The target-analyte depleted test gas, now referenced as spent gas, exits the detection assembly 170 through a channel system (not collectively numbered) in the endcap 140.

Channel System

As shown in FIGS. 4-6, a series of orifices (not collectively numbered) and channels (not collectively numbered) are provided in the sensor 100 for (i) directing test gas into operable sensing contact with the detection assembly 170, (ii) directing spent gas to "flush" the peripheral interface between the housing 120 and the endcap 140, and finally (iii) discharging the spent flush gas from the sensor 100 to atmosphere.

Referring to FIGS. 5 and 6, fluid flows through the channel system (not collectively numbered) in the following sequence:

Test gas is introduced into the chamber 129 of the sensor 100 and into sensing engagement with the detection assembly 170 through an inlet channel $129_1$ in the first end 121 of the housing 120, The test gas flows longitudinally x through the chamber 129 and into sensing engagement with the detection assembly 170 where target analyte in the test gas is detected and consumed, forming target analyte depleted spent gas, The spent gas flows within the chamber 129 to an inlet channel $149_1$ in the inner surface (unnumbered) of the endcap 140, From the inlet channel $149_1$ the spent gas flows around the periphery of the endcap 140 at the interface of the inner surface (unnumbered) of the housing 120 and the outer surface (unnumbered) of the endcap 140 within a primary annular peripheral channel $149_2$ located between inner and outer o-rings 143' and 143", and then vented to atmosphere from the endcap 140 and the lumen 128 of the housing 120 through an outlet channel $129_2$ in the endcap 140 wherein the inlet channel $149_1$ and the outlet channel $129_2$ communicate with the primary annular peripheral channel $149_2$ at radially r diametric points on the primary annular peripheral channel $149_2$, Optionally, the endcap 140 may be provided with a stagnant secondary annular peripheral channel $149_3$ located between outer and outermost o-rings 143' and 143'", and a diversion channel $149_4$ for providing fluid communication between the outlet channel $129_2$ and the secondary annular peripheral channel $149_3$ whereby any target analyte reaching the secondary annular peripheral channel $149_3$ from the surrounding environment through or past the outermost o-ring 143'" will preferentially diffuse from the secondary annular peripheral channel $149_3$ into the outlet channel $129_2$ for venting from the sensor 100 rather than through or past the outer o-ring 143" and into the primary annular peripheral channel $149_2$.

If desired, a tube (not shown) may be connected to the exhaust tube 160 for directing spent gas exiting the endcap 140 through outlet channel $129_2$ for capture and subsequent treatment or for venting from a room or building.

Use

The sensor 10 or 100 is used by pumping a gaseous sample through the sensor 10 or 100 at a known flow rate. Generally, the flow rate should be maintained between a minimum of about 2 $cm^3$/min and a maximum of about 60 $cm^3$/min—depending upon the composition and configuration of the detection assembly 70 or 170. A flow rate of less than about 2 $cm^3$/min is difficult to accurately control while a flow rate of greater than about 60 $cm^3$/min can reduce efficiency of the sensor 10 or 100 by moving target analyte through the detection assembly 70 or 170 with a velocity which limits the ability of the detection assembly 70 or 170 to detect the target analyte.

By flushing the encap(s) 40 and 50 or 140 with spent gas, introduction of contaminating target analyte from the surrounding environment into sensing contact with the detection assembly 70 or 170 is virtually eliminated. This allows the sensor 10 or 100 to accurately and reliably detect and measure concentrations of target analyte as low as 100 to 1000 ppt. To achieve such sensitivity, the detection assembly 70 or 170 should consume at least 90% of target analyte in the test gas, preferably at least 95% of target analyte in the test gas, and most preferably 99% of target analyte in the test gas, thereby forming a spent gas that is nearly devoid of any target analyte.

I claim:

1. A sensor for detecting a target analyte in a gaseous sample, comprising:
    (a) a container defining an enclosed space and having at least one access opening into the enclosed space,
    (b) a stopper sealingly engaged within each access opening, each stopper defining a peripheral interface with the container,
    (c) a target analyte detection assembly retained within the enclosed space,
    (d) an inlet and an outlet configured and arranged for introducing an externally delivered test gas into sensible engagement with the target analyte detection assembly to create spent gas, and discharging the spent gas from the target analyte detection mechanism to atmosphere, and
    (e) a channel system interconnecting the inlet and outlet and including a peripheral passageway at the interface of the container and each stopper, the channel system configured and arranged to direct spent gas through the peripheral passageways prior to discharge of the spent gas to atmosphere.

2. The sensor of claim 1 wherein the target analyte is water vapor.

3. The sensor of claim 1 wherein the target analyte is oxygen.

4. The sensor of claim 1 wherein the container is a glass tube.

5. The sensor of claim 1 wherein the container has a single first access opening.

6. The sensor of claim 1 wherein the container has a first access opening sealingly engaged by a first stopper and a second access opening sealingly engaged by a second stopper.

7. The sensor of claim 6 wherein the channel system is configured and arranged to direct the flow of spent gas in serial fashion to the peripheral passageway at each stopper.

8. The sensor of claim 6 wherein the inlet extends through the first stopper and the outlet extends through the second stopper.

9. The sensor of claim 8 wherein and the stoppers are diametrically positioned on the container.

10. The sensor of claim 1 wherein (i) each stopper is comprised of metal, (ii) each stopper includes a pair of axially spaced peripheral o-rings operable for sealingly engaging the container, and (iii) the peripheral passageway at the interface of the container and each stopper is positioned between the pair of o-rings on each stopper.

11. The sensor of claim 1 wherein the target analyte detection assembly consumes target analyte.

12. The sensor of claim 11 wherein the target analyte detection assembly is a coulometric electrochemical assembly.

13. A method of measuring the concentration of a target analyte in a test gas, comprising the steps of:
    (a) obtaining a sensor in accordance with claim 1,
    (b) effecting a continuous flow of the test gas into sensing communication with the target analyte detection assembly through the inlet in the sensor, and
    (c) measuring the concentration of the target analyte in the test gas with the target analyte detection assembly.

14. A method of measuring the concentration of a target analyte in a test gas, comprising the steps of:
    (a) obtaining a sensor in accordance with claim 11,
    (b) effecting a continuous flow of the test gas into sensing communication with the target analyte detection assembly through the inlet in the sensor, and
    (c) measuring the concentration of the target analyte in the test gas with the target analyte detection assembly,
    (d) wherein the target analyte detection assembly consumes at least 90% of target analyte in the test gas flowing through the target analyte detection assembly so as to produce spent gas having a depleted concentration of target analyte.

15. A method of claim 14 wherein the concentration of target analyte in the test gas is less than 10 ppb.

16. A method of claim 14 wherein the concentration of target analyte in the test gas is less than 1 ppb.

17. A method of claim 14 wherein the concentration of target analyte in the spent gas is less than 1 ppb.

18. A method of claim 14 wherein the concentration of target analyte in the spent gas is less than 0.1 ppb.

* * * * *